US00PP11085P

United States Patent [19]

Cunneen

[11] Patent Number: Plant 11,085

[45] Date of Patent: Oct. 12, 1999

[54] ARGYRANTHEMUM PLANT NAMED 'SUMMER ANGEL'

[75] Inventor: Thomas Michael Cunneen, Theresa Park, Australia

[73] Assignee: University of Sydney Plant Breeding Institute, Cobbitty, Australia

[21] Appl. No.: 08/938,668

[22] Filed: Sep. 26, 1997

[51] Int. Cl.[6] ..... A01H 5/00

[52] U.S. Cl. ..... Plt./263

[58] Field of Search ..... Plt./263

[56] References Cited

U.S. PATENT DOCUMENTS

P.P. 10,298 3/1998 Cunneen ..... Plt./263

*Primary Examiner*—Howard J. Locker
*Assistant Examiner*—Kent L. Bell
*Attorney, Agent, or Firm*—C. A. Whealy

[57] ABSTRACT

A distinct cultivar of Marguerite Daisy plant named Summer Angel, characterized by its upright plant habit; freely branching plant form; numerous inflorescences per plant; early flowering; large anemone-type inflorescences; and pure white ray and bright yellow disc florets.

2 Drawing Sheets

The present invention relates to a new and distinct cultivar of Marguerite Daisy plant, botanically known as *Argyranthemum frutescens* and referred to by the cultivar name 'Summer Angel'.

The new cultivar is a product of a planned breeding program conducted by the inventor in Cobbitty, New South Wales, Australia. The objective of the breeding program was to develop compact and freely-flowering Marguerite daisies that have large inflorescences and flower early.

The new cultivar originated from a cross made by the inventor in 1992 of a proprietary selection of *Argyranthemum frutescens* identified as number 20045, as the male or pollen parent, with the *Argyranthemum frutescens* cultivar 'Rosalin' (not patented), as the female or seed parent. The cultivar 'Summer Angel' was discovered and selected by the inventor as a flowering plant within the progeny of the stated cross in a controlled environment in Cobbitty, New South Wales, Australia. Compared to plants of the male parent, the selection number 20045, plants of the new Marguerite Daisy are larger and have larger inflorescences. Compared to plants of the female parent, the cultivar 'Rosalin', plants of the new Marguerite Daisy are more compact, have larger inflorescences and differ in ray floret color and inflorescence form.

Asexual reproduction of the new cultivar by terminal cuttings taken in Macquarie Fields and Cobbitty, New South Wales, Australia, has shown that the unique features of this new Marguerite Daisy are stable and are reproduced true to type in successive propagations.

The new cultivar has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Summer Angel' which distinguish 'Summer Angel' as a new and distinct cultivar:

1. Upright plant habit.
2. Freely branching plant form.
3. Numerous inflorescences per plant.
4. Early flowering.
5. Large anemone-type inflorescences.
6. Pure white ray and bright yellow disc florets.

Plants of the new Marguerite Daisy can be compared to plants of the cultivar 'Compacta' (not patented). In side-by-side comparisons conducted in Cobbitty, New South Wales, Australia, plants of the new Marguerite Daisy were taller and differed in inflorescence form. Additionally plants of the new Marguerite Daisy had larger inflorescences and thinner, longer leaves than plants of the cultivar 'Compacta'.

Plants of the new Marguerite Daisy can also be ompared to plants of the cultivar 'Sugar Baby' (disclosed in U.S. Plant Pat. No. 10,298). In side-by-side comparisons conducted in Encinitas, Calif., plants of the new Marguerite Daisy were taller, less spreading, more open, more vigorous, and had a different inflorescence form. Additionally plants of the new Marguerite Daisy had larger leaves and larger inflorescences than plants of the cultivar 'Sugar Baby'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph on the first sheet comprises a side perspective view of a typical container plant of 'Summer Angel'.

The photograph on the second sheet comprises a close-up view of typical inflorescences of 'Summer Angel'. Floret and foliage colors in the photographs may appear different from the actual colors due to light reflectance.

DETAILED BOTANICAL DESCRIPTION

The following observations, measurements and values describe plants grown in Encinitas, Calif. in a polyethylene-covered greenhouse with day and night temperatures averaging 24 and 15° C., respectively. Color references are made to The Royal Horticultural Society Colour Chart except where general terms of ordinary dictionary significance are used.

Botanical classification: *Argyranthemum frutescens* cultivar 'Summer Angel'.

Parentage:

*Male or pollen parent.*—Seedling selection of *Argyranthemum frutescens*, identified as number 20045.

*Female or seed parent.*—*Argyranthemum frutescens* cultivar 'Rosalin' (not patented).

Propagation:

*Type cutting.*—Terminal cuttings.

*Time to initiate and develop roots.*—About 10 or 14 days at temperatures of 26 or 18° C., respectively.

*Rooting habit.*—Numerous, fibrous, and freely branching.

Plant description:

*General appearance.*—Upright and inverted triangle. Loose and rangy herbaceous plant with pinnatifid foliage and erect flower stems that hold the inflorescences above the foliage. Appropriate for various sizes and types of containers.

*Plant height.*—About 55 cm from soil level to top of inflorescences.

*Plant width.*—About 38 cm.

*Branching.*—Freely branching, plants usually do not require pinching.

*Vigor.*—Vigorous.

*Internode length.*—About 1.2 cm.

*Stem color.*—144B.

*Foliage description.*—Arrangement: Alternate, single. Shape: Pinnatifid. Apex: Acute. Base: Attenuate, sessile. Margin: Deeply incised. Length: About 9 cm. Width: About 4 cm. Texture: Glabrous and smooth. Durability to stresses: Good. Color: Young leaves, upper surface: 138A. Young leaves, lower surface: 137D. Mature leaves, upper surface: 137A. Mature leaves, lower surface: 137B. Venation, upper surface: 137A. Venation, lower surface: 137B.

Flowering description:

*Flowering habit.*—Single anemone-type composite inflorescence form. Inflorescences form at upper leaf axils. Florets arranged acropetally on a capitulum. Inflorescences last about one week.

*Quantity of inflorescences.*—Freely flowering, typically 5 to 6 flowers per lateral stem. Usually more than 50 inflorescences in flower per plant.

*Natural flowering season.*—Natural flowering season is spring to early fall. Plants flower continuously during this period.

*Inflorescence diameter.'*About 4.7 cm.

*Inflorescence depth* (*height*).—About 1.2 cm.

*Fragrance.*—None.

*Ray florets.*—Appearance: Satiny. Aspect: Flat. Shape: Elliptic. Apex: Tri-dentate. Base: Attenuate. Margin: Entire. Length: About 2.2 cm. Width: About 6 mm. Texture: Smooth, glabrous. Color:

When opening and mature, both surfaces: 155D. Number of ray florets per inflorescence: About 22 in two rows.

*Disc florets.*—Shape: Tubular, 5-parted and flared at apex. Diameter of disc: About 1.8 cm. Disc floret length: About 7 mm. Disc floret width: About 1 mm. Color: Immature: 151B. Mature: 13A/14A becoming white, 155D at apex, 3B at base. Number of disc florets per inflorescence: Numerous, usually about 175.

*Phyllaries.*—Arrangement: Imbricate, alternate rows; tightly pressed to the receptacle. Shape: Elliptic. Length: About 6 mm. Diameter: About 8 mm.

*Peduncle.*—Length: First peduncle: About 8 cm. Fourth peduncle: About 12 cm. Strength: Moderately strong and erect, inflorescences held above foliage. Texture: Smooth. Color: 144A.

*Flower bud.*—Shape: Spherical. Length: About 7 mm. Diameter: About 6 mm. Color: 157A.

*Androecium.*—Present on disc florets only. Anther color: 14A. Pollen color: 14A. Amount of pollen: Low.

*Gynoecium*—Present on ray and disc florets. Pistil number: One per floret. Pistil length: About 4 mm. Style length: About 3 mm. Style color: 1C. Stigma shape: Bipartate. Stigma color: 12A. Ovary color: 1C.

Disease resistance: No resistance to fungal, bacterial or viral pathogens has been noted.

Seed production: Seed production is typically not observed.

It is claimed:

1. A new and distinct Marguerite Daisy plant named 'Summer Angel', as illustrated and described.

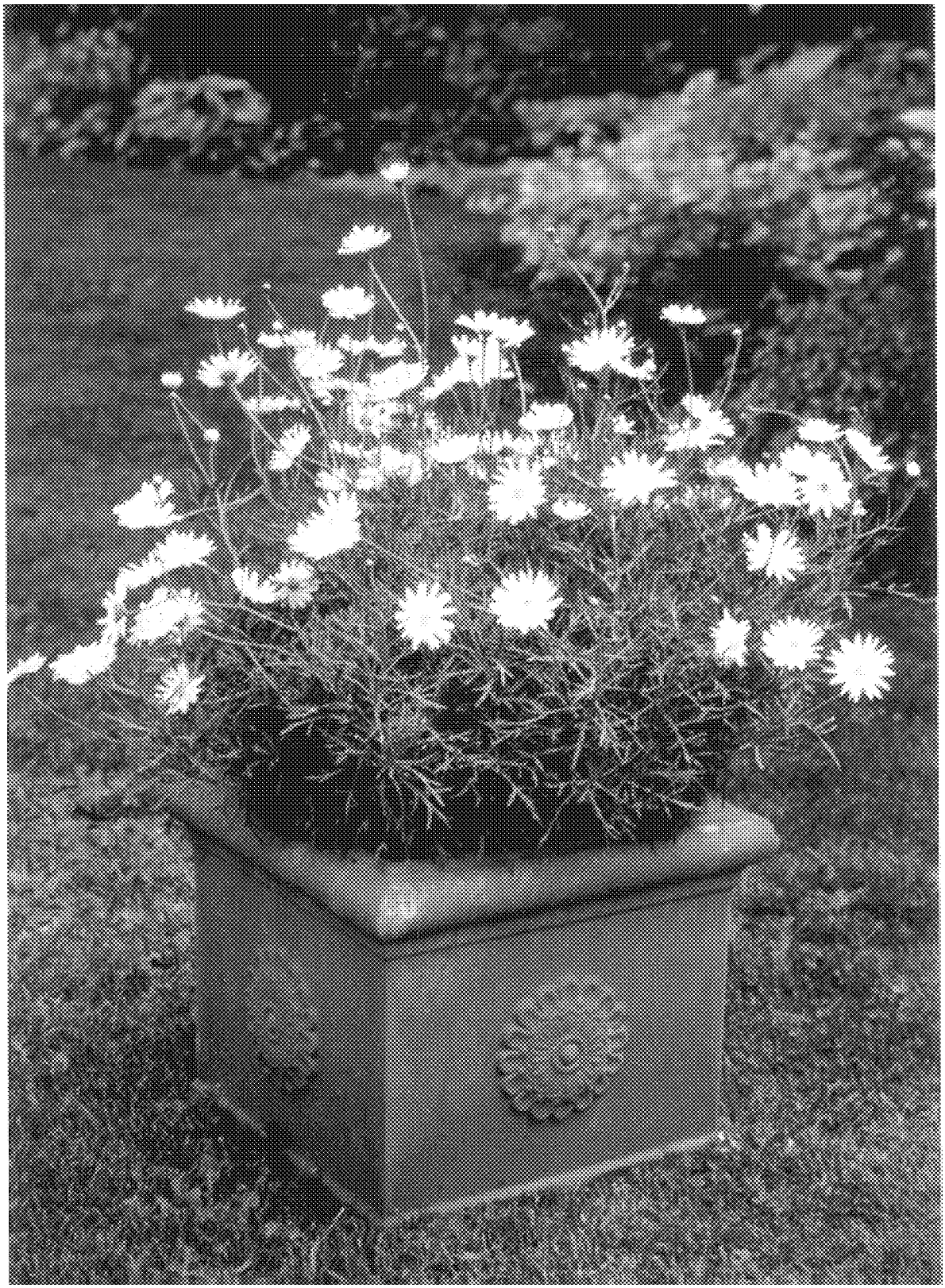

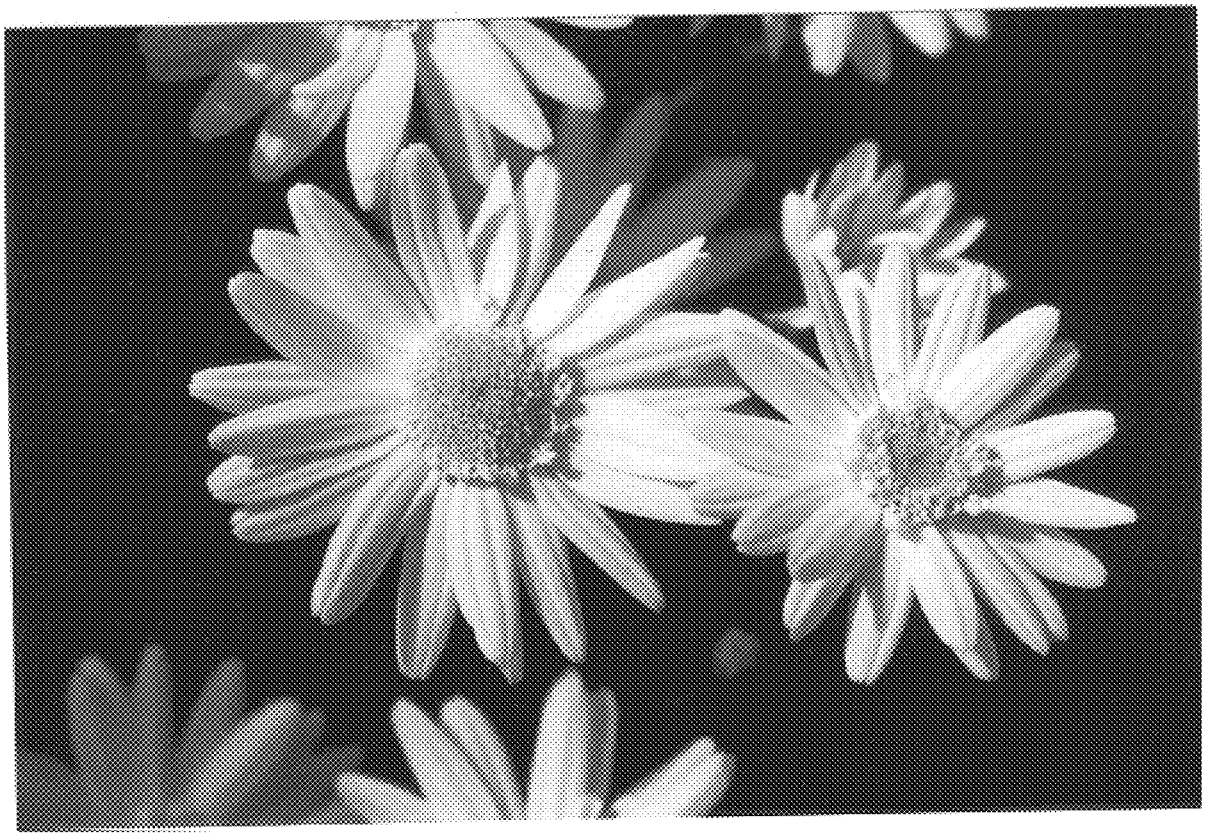

* * * * *